United States Patent [19]
Mitsumaki et al.

[11] Patent Number: 5,320,966
[45] Date of Patent: Jun. 14, 1994

[54] METHOD FOR ANALYZING SAMPLES AND AUTOMATIC PROCESSOR THEREFOR

[75] Inventors: Hiroshi Mitsumaki, Mito; Fujiya Takahata, Katsuta, both of Japan

[73] Assignee: Hitachi, Ltd., Tokyo, Japan

[21] Appl. No.: 752,200

[22] Filed: Aug. 21, 1991

Related U.S. Application Data
[63] Continuation of Ser. No. 268,988, Nov. 9, 1988, abandoned.

[30] Foreign Application Priority Data
Nov. 13, 1987 [JP] Japan .................. 62-285396

[51] Int. Cl.$^5$ .................................... G01N 35/02
[52] U.S. Cl. .................................... 436/47; 436/50; 436/55; 422/63; 422/64; 422/68.1; 422/116
[58] Field of Search .................. 422/63–65, 422/77, 68.1; 436/47, 48, 50, 51, 55; 364/184, 188

[56] References Cited
U.S. PATENT DOCUMENTS
| | | | |
|---|---|---|---|
| 3,883,306 | 5/1975 | Widen | 422/64 |
| 4,090,791 | 5/1978 | Siddigi et al. | 356/184 |
| 4,522,921 | 6/1985 | Ogawa | 422/65 |
| 4,849,176 | 7/1989 | Sakagami | 422/65 |

FOREIGN PATENT DOCUMENTS
| | | |
|---|---|---|
| 0078948 | 5/1983 | European Pat. Off. . |
| 55-21303 | 6/1980 | Japan . |
| 59-22905 | 5/1984 | Japan . |
| 59-24380 | 6/1984 | Japan . |
| 2009401 | 6/1979 | United Kingdom . |
| 8802866 | 4/1988 | World Int. Prop. O. . |

Primary Examiner—James C. Housel
Assistant Examiner—Jeffrey R. Snay
Attorney, Agent, or Firm—Fay, Sharpe, Beall, Fagan, Minnich & McKee

[57] ABSTRACT

An automatic processor for analyzing reaction solutions has a large number of reaction vessels arranged in a circle on a disk, a disk driver for circulating the reaction vessels successively to pass through a sample pouring position, a reagent adding position and an analyzing position in order, sample pouring pipet nozzle for pouring a sample into each of the reaction chambers at the sample pouring position, reagent adding pipet nozzle for adding a reagent into each of the reaction chambers at the reagent adding position, and analyzer for analyzing a reaction solution in each of the reaction vessels at the analyzing position. A large number of reaction vessels are divided into a plurality of reaction vessel groups each of which has a plurality of reaction vessels. The disk driver circulates each of the reaction vessel groups in a predetermined time in accordance with the reaction times of the reaction solutions in the reaction vessels of the same reaction vessel group.

11 Claims, 3 Drawing Sheets

METHOD FOR ANALYZING SAMPLES AND AUTOMATIC PROCESSOR THEREFOR

This application is a continuation of application Ser. No. 07/268,988 filed Nov. 9, 1988, now abandoned.

FIELD OF THE INVENTION AND RELATED ART STATEMENT

The present invention relates to a method for analyzing samples and to an automatic processor for analyzing samples and, more particularly, to an automatic processor which is capable of conducting various analyzing operations with different times required for the reaction between the sample and a reagent to be completed, that is, or different reaction times.

There has been proposed a single reaction line-multianalyzing apparatus, as disclosed in Japanese Patent Examined Publication No. 55-21303. This apparatus has a reagent supply section, an analysis section provided with a multiwave photometer, and a single reaction line extending between these two sections. A plurality of reaction chambers are arranged on the single reaction line. The reaction chambers in which different reactions are effected separately are forwarded successively to the analysis section. In the analysis section, a reaction solution in each of the reaction chambers is analyzed by means of the multiwave photometer. This technique makes it possible to reduce the size of the apparatus.

In general, the reaction time varies according the analysis items. Namely, the time required for the reaction chamber to be moved from a reagent adding position to an analyzing position must be adjusted in accordance with the analysis items (reaction times). For this reason, in the above-described prior art, the reagent adding position is changed in accordance with the analysis items so as to adjust the reaction time. Therefore, it is necessary to provide a large number of reagent adding mechanisms (or various reagent adding positions).

Meanwhile, there is disclosed a reagent pipetting device in Japanese Patent Examined Publication No. 59-22905. This device enables the addition of many kinds of reagents to be ensured with a simple construction.

According to this device, however, every reagent is needed to be added into the reaction chamber at the same position on the single reaction line. Therefore, this device can be applicable to analysis items having the reaction times which are identical with each other but cannot be applied to analysis items having reaction times which are different from each other.

OBJECT AND SUMMARY OF THE INVENTION

It is therefore one object of the present invention to provide a method for analyzing samples in which the reagent is added to the sample at the same position on a reaction line even if the reaction times for the respective analysis items are different from each other. Further, it is another object of the present invention to provide an automatic processor which is capable of performing the above method.

To this end, according to the present invention, provided is an automatic processor in which reaction chambers in each of a plurality of reaction chamber groups are made to circulate successively to pass through a sample pouring position, a reagent adding position and an analyzing position in the mentioned order, in accordance with the reaction times of the reaction solution in the reaction chambers of the reaction chamber groups.

Other objects, effects and functions of the present invention will become more clear from the following description of the preferred embodiments with referring to the accompanying drawings.

DETAILED DESCRIPTION OF PREFERRED EMBODIMENTS

Figure 1:
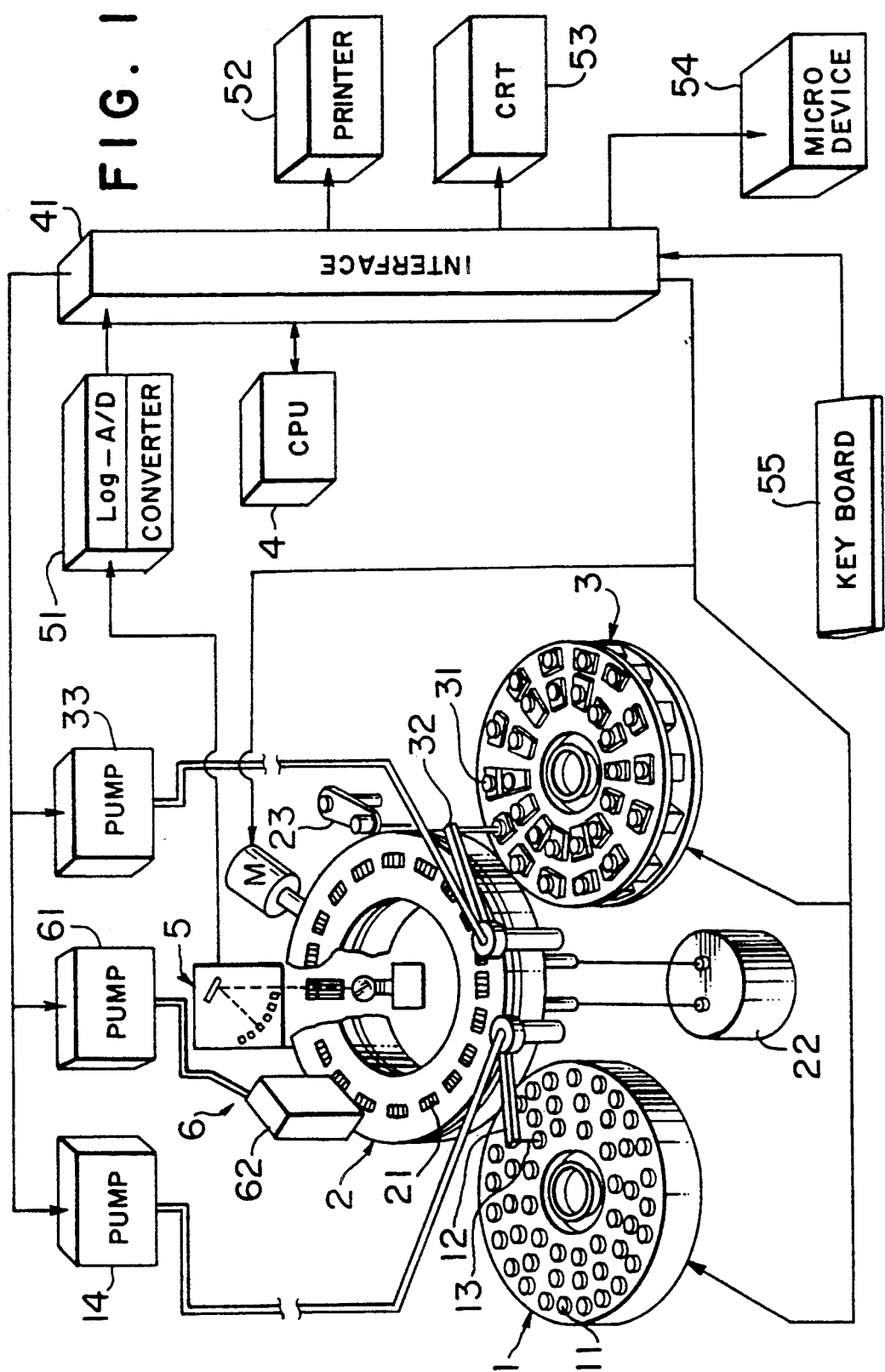
FIG. 1 is a perspective view showing the whole of an embodiment of the present invention.

Referring to FIG. 1, an automatic processor of an embodiment of the present invention comprises a sample disk 1, a reaction disk 2, and a reagent disk 3. A plurality of sample cups 11 are disposed in the sample disk 1. The sample cups 11 accommodate samples therein. Also, a plurality of reagent cups 31 are disposed in the reagent disk 3. Different reagents are accommodated in the reagent cups 31 separately.

One hundred and twenty (120) reaction vessels 21 are arranged circularly in the reaction disk 2. The reaction vessels 21 are divided or classified into thirty (30) reaction vessel groups I-XXX, each of which includes four (4) reaction vessels 21. Temperature of the respective reaction vessels 21 is maintained at 37° C. by a constant temperature bath 22.

A CPU 4 sends a command signal to a drive motor M for the reaction disk 2 through an interface 41 to rotatively drive the disk 2 in a controlled manner. The CPU 4 also sends command signals to the disks 1 and 3 to rotate them.

In association with the sample disk 1, a sample pipetting arm 12 having a pipetting nozzle 13 is provided so as to be swingable about an axis thereof so that it is allowed to move in a swinging motion between the sample cup 11 in the sample disk 1 and the reaction vessel 21 in the reaction disk 2, which is located at the sample receiving position. A pump 14 is connected to the pipetting arm 12 to cause the latter to draw the sample from the sample cup 11 and then pour the same into the reaction vessel 21. The swinging motion of the sample pipetting arm 12 and the operation of the pump 14 are controlled by the CPU 4.

A reagent pipetting arm 32 is provided, in association with the reagent disk 3, so as to be swingable about an axis thereof so that it is allowed to move in swinging motion between the reagent cup 31 in the reagent disk 3 and the reaction vessel 21 in the reaction disk 2, which is located at the reagent receiving position. A pump 33 is connected to the reagent pipetting arm 32 so as to cause the latter to draw the reagent from the reagent cup 31 and then add the same into the reaction vessel 21. The swinging motion of the reagent pipetting arm 32 and the operation of the pump 33 are controlled by the CPU 4.

Next, operation of the automatic processor having the above-described arrangement will be described hereinunder.

First, the sample pipetting arm 12 draws a sample from the sample cup 11 in the sample disk 1. Then, the sample pipetting arm 12 moves in swinging motion to the sample pouring position and pours the sample into a reaction vessel 21A of a first reaction vessel group I of the reaction disk 2. After one cycle time (thirty (30) seconds, in this embodiment) has elapsed, the reaction disk 2 is rotated counterclockwise such that one of the reaction vessels 21 of a second reaction vessel group II adjacent to the first reaction vessel group I is located at the sample pouring position.

After four cycle times (two (2) minutes) have elapsed, the reaction vessel 21A of the first reaction vessel group I reaches the reagent adding position. In advance of this the reagent pipetting arm 32 has sucked a reagent, which is associated with the sample in the reaction vessel 21A, from one of the reagent cups 31 in the reagent disk 3 and, then, swung to the reagent adding position.

When the reaction vessel 21A of the first reaction vessel group I arrives at the reagent adding position, the reagent pipetting arm 32 is operated to add the reagent into the reaction vessel 21A.

After five cycle times (two (2) minutes and thirty (30) seconds) have elapsed, the reaction disk 2 is further rotated so that the reaction vessel 21A arrives at a stirring position. At this position, the reaction solution in the reaction vessel is stirred by a stirrer 23 so as to be made uniform.

Thereafter, the reaction vessel 21A reaches an analyzing position. At the analyzing position, the reaction solution in the reaction vessel 21A is analyzed by a multiwave photometer 5. A signal indicative of the quantity of transmitted light read by the multiwave photometer 5 is digitalized on an absorbancy scale by means of a Log converter/AD converter 51. A digital signal from the Log converter/AD converter 51 is read into the CPU 4 through the interface 41. The CPU 4 operates to convert the read digital signal indicative of the absorbancy into concentration data. Output of this data is provided to a printer 52 or a CRT 53. In addition, the data can also be stored in a microdevice 54 according to the operation of a keyboard 55.

At a washing position beyond the analyzing position, in the case that the reaction in the reaction vessel has been completed, the reaction solution in the reaction vessel is discharged. The reaction vessel is washed by a washing device 6 constituted by a washing pump 61 and a washing nozzle 62 and then placed at the service of the coming reaction. However, in the case that the reaction in the reaction vessel has not been completed during the movement of the reaction vessel from the reagent adding position to the analyzing position (such condition can be foreseen by the CPU 4 from the kind of the reagent to be added), the CPU 4 operates to render the washing pump 61 inoperative through the interface 41. Therefore, discharge of the reaction solution and washing of the reaction vessel are not performed. In this case, the reaction vessel which contains the reaction solution is moved to reach again the sample pouring region. Upon the confirmation of the fact that the reaction has not been finished in the reaction vessel, the CPU 4 operates the drive motor M to rotate the reaction disk 2 such as to allow another empty reaction vessel of the reaction vessel group to be located at the sample pouring position, which group includes the thus confirmed reaction vessel.

The operations described hereinabove are repeated for each reaction vessel group.

The above-described procedure for pouring of the sample will be explained in detail hereinunder with reference to FIGS. 2A to 2D.

Figure 2A:
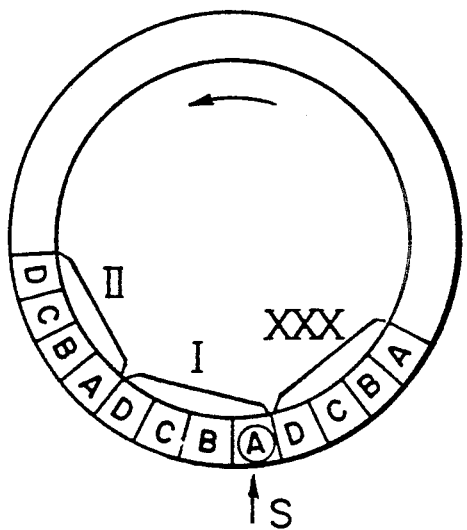
FIGS. 2A to 2D are charts illustrating the procedure for the pouring of the sample into the reaction vessels of the embodiment shown in FIG. 1.

Referring to FIG. 2A, a hundred and twenty (120) reaction vessels on the reaction disk are divided or classified into thirty (30) reaction vessel groups I to XXX each having four reaction vessels and distinguished from one another. References A, B, C and D are separately put to the four reaction vessels of each reaction vessel group to discriminate them from each other.

Figure 2B:
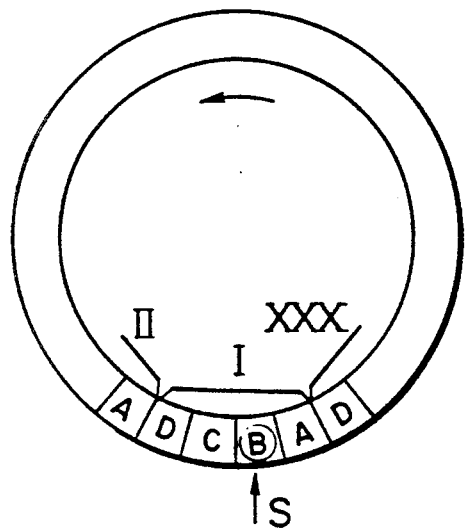
Figure 2C:
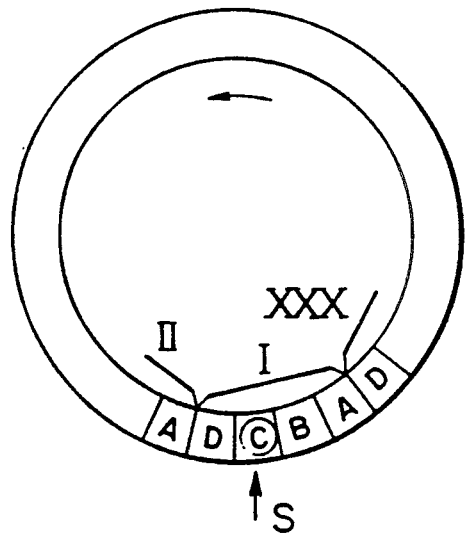
Figure 2D:
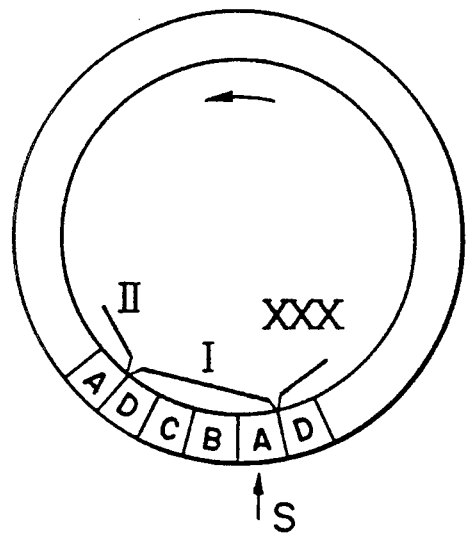

As the reaction disk 2 is rotated, samples used for the reactions, the reaction times for which are different from each other, are poured into the separate reaction vessels A to C in one of the reaction vessel groups one by one at the sample pouring position S (see FIGS. 2A to 2C). First, a sample is poured into a reaction vessel A of the reaction vessel group I, for example (see FIG. 2A). Then, the reaction disk 2 is rotated counterclockwise so that a reaction vessel A of the next reaction vessel group II is located at the sample pouring position S. A sample is poured into the reaction vessel A of the reaction vessel group II as well. A period of time required between the pouring of the sample into the reaction vessel A of the reaction vessel group I and the pouring of the sample into the reaction vessel A of the reaction vessel group II is referred to as one cycle time. In this case, such period is thirty (30) seconds. With the rotation of the reaction disk 2, a reagent α related to a reaction time corresponding to the time duration of three rotations of the disk 2, i.e. about forty-five minutes, is added into the reaction vessel A of the reaction vessel group I at the reagent adding position, and the reaction vessel A of the reaction vessel group I is further moved to the analyzing position. Since the time required for the reaction vessel A to move from the reagent adding position to the analyzing position is less than fifteen minutes, the reaction in the reaction vessel A has not been completed. Therefore, the reaction disk 2 is further rotated to make the reaction vessel A return again to the sample pouring region without being subjected to analysis and washing. Since the CPU recognizes that the reaction vessel A of the reaction vessel group I contains the reaction solution, the CPU operates to control the rotation of the reaction disk in such a manner that an empty reaction vessel of the reaction vessel group I or a reaction vessel B, for example, is located at the sample pouring position S (see FIG. 2B). Then, a sample is poured into the reaction vessel B of the reaction vessel group I as well. A reagent β related to a reaction time corresponding to the time duration of two rotations of the disk 2, i.e. about thirty minutes, is added into the reaction vessel B at the reagent adding position. The time required for the reaction vessel B to move from the reagent adding position to the analyzing position is also less than fifteen minutes so that the reactions in the reaction vessels A and B have not been completed. Therefore, the reaction disk 2 is further rotated to make the reaction vessels A and B return again to the sample pouring region without being subjected to analysis and washing. Since the CPU recognizes each of the reaction vessels A and B of the reaction vessel group I contain the reaction solution, the CPU operates to control the rotation of the reaction disk in such a manner that an empty reaction vessel of the reaction vessel group I or a reaction vessel C, for example, is located at the sample pouring position S (see FIG. 2C). Then, a sample is poured into the reaction vessel C of the reaction vessel group I as well. A reagent γ related to a reaction time corresponding to the time duration of one rotation of the disk 2, i.e. about fifteen minutes is added into the reaction vessel C at the reagent adding position. During the time required for the reaction vessel C to move from the reagent adding position to the analyzing position, all of the reactions in the reaction vessels A, B and C are completed simultaneously. Namely, the reaction times in connection with the reagents α and β are equal to integral multiples of the reaction time in connection with the reagent γ. After all of the reactions have been completed, these reaction vessels A, B and C are forwarded to the analyzing position where the respective reaction solutions are analyzed. Thereafter, these reaction vessels A, B and C are moved to the washing position and subjected to washing to be prepared for the coming reaction. FIG. 2D shows the state of the empty reaction vessel A of the reaction vessel group I returned back to the sample pouring position S.

As has been described hereinabove, it is designed according to the present invention that, although each reaction vessel group including four reaction vessels repeats movement and stops as a unit for every cycle time, an empty reaction vessel in the subjective reaction vessel group is selected and is allowed to be located at the sample pouring position. In consequence, it is possible to process a plurality of reaction systems with different reaction times. A method according to which analyzing operations with different reaction times can be conducted on a single reaction line is called "a single reaction line-random access method".

Figure 3:
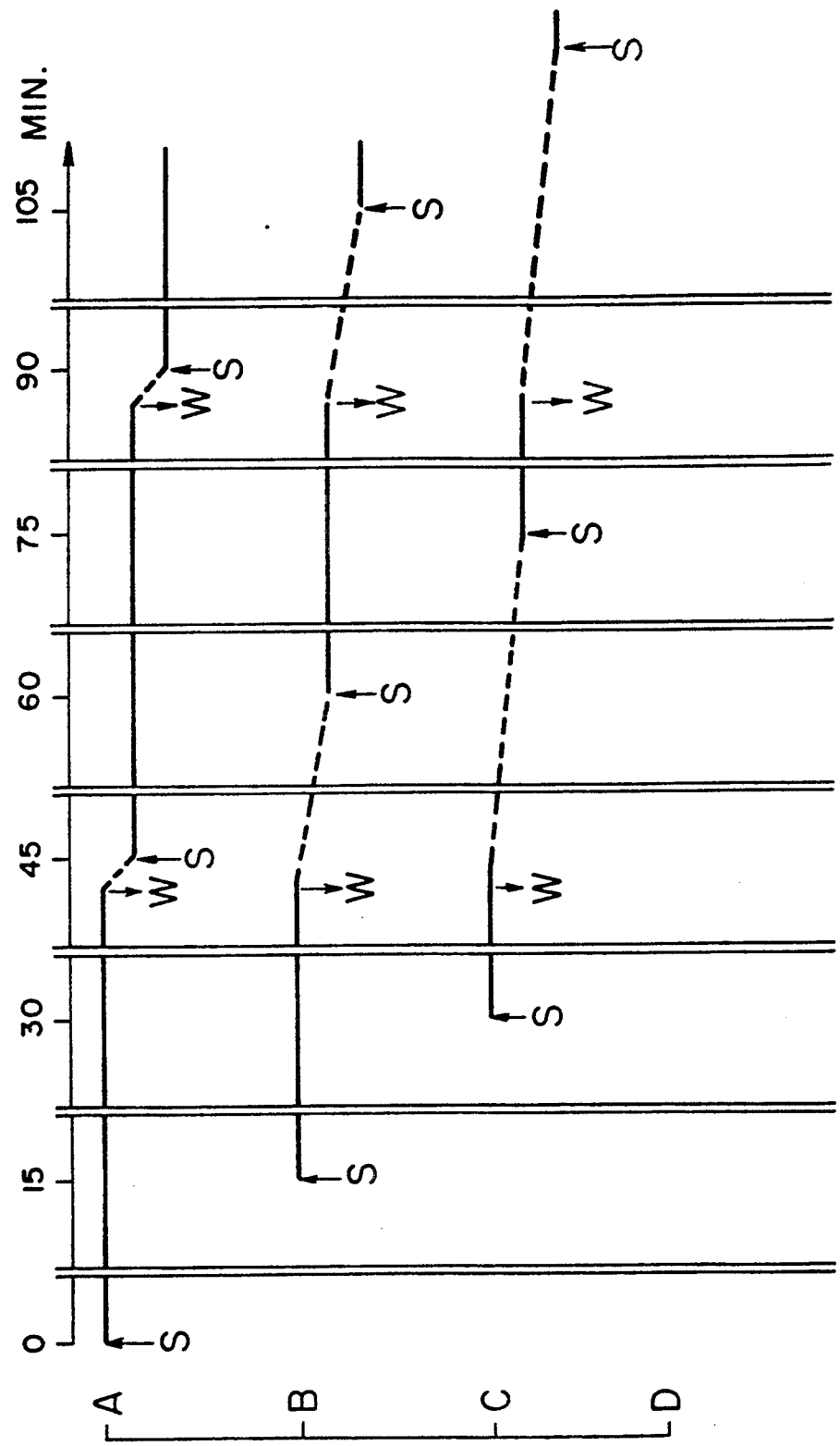
FIG. 3 is a time chart showing the relationship between the timing of pouring of the sample into the reaction vessels and the timing of washing of the reaction vessels.

FIG. 3 is a time chart showing the relationship between the timing of pouring of the sample into the reaction vessels and the timing of washing of the reaction vessels. References A to C denote the reaction vessels respectively, a reference S denotes the timing of pouring of the sample, and a reference W denotes the timing of discharge of the reaction solution from the reaction vessel and washing of the reaction vessel. Each time the reaction disk makes one rotation, the sample is poured into the empty reaction vessel for each of the reaction vessel groups.

In the above-described embodiment, since the reaction times for the respective reaction vessels in the same reaction vessel group are set to be equal to integral multiples of the minimum one among them, all of the reactions can be completed simultaneously. Therefore, discharge of the reaction solutions and washing of the reaction vessels can be carried out simultaneously. This contributes to easy handling of the apparatus.

Next, description will be given of another embodiment.

In the above-described embodiment, it is designed that, upon the confirmation of the empty reaction vessel of each reaction vessel group, the CPU 4 operates to control the rotation of the reaction disk so as to allow the empty reaction vessel to be located at the predetermined sample pouring position. However, in this another embodiment, the reaction vessels of each reaction vessel group are located in the predetermined sample region and the pipetting nozzle 13 of the sample pipetting arm 12 is controlled to be moved toward an empty reaction vessel of such reaction vessel group which has recognized by the CPU 4. Namely, in this another embodiment, the sample pouring region is not changed but the sample pouring position is changed in accordance with the location of the empty reaction vessel. Since the sample pouring region is stationary (that is, the time duration of stoppage of the, reaction disk at the sample pouring position is not changed), other operations (such as addition of the reagent, stirring, analysis and washing) can be positively carried out during such time duration.

Next, description will be given of still another embodiment.

In this embodiment as well, the construction thereof is the same as that of the above-described two embodiments. In this embodiment, it is designed that, after the sample is poured into the reaction vessel of the reaction vessel group I, the reaction disk is caused to make one rotation and, further, rotate slightly in the same direction such as to allow the reaction vessel of the adjacent reaction vessel group II to be located at the sample pouring position within one cycle time (which is very long as compared with the aforementioned one cycle time). Alternatively, after the sample is poured into the reaction vessel of the reaction vessel group I, the reaction disk is caused to rotate in a manner to be short of a full rotation within one cycle time so that one reaction vessel of the adjacent reaction vessel group XXX is located at the sample pouring position. Accordingly, all of the reaction vessels are made to pass through the analyzing position within one cycle time. In consequence, it is possible to know the change with the lapse of time of the reaction in each of the reaction vessels until the reaction is completed. The present embodiment is suitable for use particularly in investigation of the reaction speed of an enzyme.

What is claimed is:

1. A method for analyzing reaction solutions in reusable reaction vessels that are washed after analysis of a reaction solution contained therein, said method comprising the steps of:

dividing said reaction vessels into a plurality of reaction vessel groups, each said group having at least three said reaction vessels;

driving each of said reaction vessels along a single closed loop through sample pouring, reagent adding, reaction solution analyzing and vessel washing positions;

assigning each of said reaction vessels of a group to have different fixed reaction times including at least one of said reaction times being less than a predetermined interval of time and all others of said reaction times being greater than said predetermined interval of time;

pouring a sample into a predetermined one of said reaction vessels of said reaction vessel groups each time the predetermined time interval elapses; and controlling said driving so that an empty one of said reaction vessels of one of said reaction vessel groups is located at the sample pouring position, and an empty one of said reaction vessels of a following one of said reaction vessel groups is located at the sample pouring position after a pouring of a sample into the one reaction vessel of the one reaction vessel group;

performing a subsequent washing of said reaction vessels at said vessel washing position after analyzing reaction solution in said reaction vessels at said analyzing position.

2. A method for analyzing reaction solution in a row of reaction vessels, said method comprising the steps of:

dividing said reaction vessels into a plurality of reaction vessel groups, each said group having a fixed number of said reaction vessels;

intermittently driving each of said reaction vessels along a closed loop in a constant predetermined interval of time for each pass of the loop through sample pouring, reagent adding, reaction solution analyzing and vessel washing positions;

performing consecutive sample pouring and reagent adding steps each time one of said reaction vessel groups passes said sample pouring and said reagent adding positions, respectively, to form reaction solutions having one of a plurality of different fixed corresponding reaction times including at least a first reaction time greater than said predetermined interval of time and a second reaction time not more than said predetermined interval of time in one of said reaction vessels of each of said reaction vessel groups, and performing a subsequent washing of said reaction vessels at said vessel washing position after analyzing said reaction solutions at said analyzing position;

controlling said washing to wash reaction vessels at said vessel washing position only after the fixed corresponding reaction time for the reaction solution contained therein has elapsed; and controlling said pouring and adding so that when a first of said reaction vessels of one said reaction vessel group containing a reaction solution having said first reaction time is driven to said pouring and said adding positions, respectively, before said first reaction time has elapsed, a second of said reaction vessels within said one reaction vessel group receives a sample and a reagent in said sample pouring and said reagent adding steps, respectively, to form a reaction solution having said second reaction time.

3. A method for analyzing reaction solutions according to claim 2, wherein said dividing includes dividing said reaction vessels so that each said reaction vessel group has four reaction vessels and so that there are thirty reaction vessel groups in total.

4. A method for analyzing reaction solutions according to claim 2, wherein said controlling of said washing includes determining the fixed corresponding reaction time for the reaction solutions contained in the reaction vessels from the type of reagent added in said reagent adding step.

5. A method for analyzing reaction solutions according to claim 2, wherein said intermittently driving each of said reaction vessels includes driving said reaction vessels one step at a time along the closed loop by a distance separating adjacent reaction vessels in the loop.

6. A method for analyzing reaction solutions in a row of reaction vessels, said method comprising the steps of:
dividing said reaction vessels into a plurality of reaction vessel groups, each said group having a fixed number of said reaction vessels;

intermittently driving each of said reaction vessels along a closed loop in a predetermined interval of time for each pass of the loop through sample pouring, reagent adding, reaction solution analyzing and vessel washing positions;

performing consecutive sample pouring and reagent adding steps each time one of said reaction vessel groups passes said sample pouring and said reagent adding regions, respectively, to form reaction solutions having one of a plurality of fixed reaction times including at least a first reaction time greater than said predetermined interval of time and a second reaction time not more than said predetermined interval of time in one of said reaction vessels of each of said reaction vessel groups, and performing a subsequent washing of said reaction vessels at said vessel washing region after analyzing said reaction solutions at said analyzing region;

controlling said washing to wash reaction vessels at said reaction vessel washing region only after the fixed reaction time for the reaction solution contained therein has elapsed; and controlling said pouring and adding so that when a first of said reaction vessels containing a reaction solution having said first reaction time of one said reaction vessel group is driven to said pouring and said adding regions, respectively, before said first reaction time has elapsed, a second of said reaction vessels within said one reaction vessel group receives a sample and a reagent in said sample pouring and reagent adding steps, respectively, to form a reaction solution having said second reaction time.

7. A method for analyzing reaction solutions according to claim 6, wherein said sample pouring and reagent adding steps are performed with pipettes movable between adjacent ones of said reaction vessels within each of said reaction vessel groups positioned within a respective one of said sample pouring and reagent adding regions.

8. A method for analyzing reaction solutions in a row of reaction vessels, said method comprising the steps of:
dividing said reaction vessels into a plurality of reaction vessel groups, each said group having a fixed number of said reaction vessels;

intermittently driving each of said reaction vessels along a closed loop in a constant predetermined interval of time for each pass of the loop through sample pouring, reagent adding, reaction solution analyzing and vessel washing positions;

performing consecutive sample pouring and reagent adding steps each time one of said reaction vessel groups passes said sample pouring and said reagent adding positions, respectively, to form reaction solutions having one of a plurality of fixed corresponding reaction times in one of said reaction vessels of each of said reaction vessel groups, and performing a subsequent washing of said reaction vessels at said vessel washing position after analyzing said reaction solutions at said analyzing position;

controlling said reagent adding step to add one of at least a first reagent having a first fixed reaction time and a second reagent having a fixed reaction time less than said first fixed reaction time to said reaction vessels, wherein said first reaction time is greater than said constant predetermined interval of time and said second reaction time is not more than said constant predetermined interval of time;

controlling said washing to wash reaction vessels at said vessel washing position only after the fixed corresponding reaction time for the reaction solution contained therein has elapsed; and controlling said reagent adding so that when a first of said reaction vessels of one said reaction vessel group is driven to said reagent adding position, a reagent is added to form a reaction solution having said first reaction time therein, and when said first reaction vessel is thereafter driven along one pass of said loop to arrive at said sample pouring and said reagent adding positions, respectively, before said first reaction time has elapsed, a second of said reaction vessels within said one reaction vessel group receives a sample and a reagent having said second reaction time in said sample pouring and said reagent adding steps, respectively, to form a reaction solution having said second reaction time.

9. An automatic analyzing method according to claim 8, wherein one of said plurality of reaction times is a minimum reaction time and the others of said plurality of reaction times are an integral multiple of said minimum reaction time.

10. An analyzing processor, comprising:
  a reaction table supporting a row of reaction vessels, said row of reaction vessels being divided into a plurality of reaction vessel groups, each said group having a fixed number of said reaction vessels;
  means for driving each of said reaction vessels along a closed loop in a constant predetermined interval of time for each pass of the loop through sample pouring, reagent adding, reaction solution analyzing and vessel washing positions;
  means for pouring in a sample and means for adding a reagent to a predetermined one of said reaction vessels of each said reaction vessel group each time said reaction vessel groups pass said sample pouring and said reagent adding positions, respectively, to form reaction solutions therein having corresponding fixed reaction times including at least first and second reaction times wherein said first reaction time is greater than said predetermined interval of time and said second reaction time is not more than said predetermined interval of time;
  means for washing said reaction vessels at said vessel washing position;
  means for analyzing said reaction solutions at said analyzing position;
  means for controlling said washing means to wash reaction vessels at said vessel washing position only after said fixed reaction time for the reaction solution contained therein has elapsed; and
  means for controlling said sample pouring means and said reagent adding means so that when a first of said reaction vessels containing a reaction solution having said first reaction time of one said reaction vessel group is driven to said pouring and said adding positions, respectively, before said first reaction time has elapsed, said sample pouring and said reagent adding means pours in a sample and adds a reagent to a second of said reaction vessels within said one reaction vessel group, respectively, to form a reaction solution in said second reaction vessel having said second reaction time.

11. An apparatus for analyzing reaction solutions in reusable reaction vessels that are washed after analyzing a reaction solution contained therein, comprising:
  means for supporting a row of said reaction vessels, said reaction vessel being divided into a plurality of reaction vessel groups, each said group having at least three said reaction vessels;
  means for driving each of said reaction vessels along a single closed loop through sample pouring, reagent adding, reaction solution analyzing and vessel washing positions, each of said reaction vessels of a group being designated for receiving reaction solutions having different fixed reaction times including at least one of said reaction times being less than a predetermined interval of time and all others of said reaction times being greater than said predetermined interval of time;
  means for pouring a sample into a predetermined one of said reaction vessels of one said reaction vessel group each time the predetermined time interval elapses;
  means for controlling said driving means so that an empty one of said reaction vessels of one of said reaction vessel groups is located at the sample pouring position, and so that an empty one of said reaction vessels of a following one of said reaction vessel groups is located at the sample pouring position after a pouring of a sample into the one reaction vessel of the one reaction vessel group;
  means for analyzing the reaction solution in said reaction vessels at the reaction solution analyzing position; and
  means for washing said reaction vessels at said vessel washing position.

* * * * *